US007435372B2

(12) United States Patent
Mimnaugh et al.

(10) Patent No.: US 7,435,372 B2
(45) Date of Patent: Oct. 14, 2008

(54) LIQUID BATH ANNEALING OF POLYMERS FOR ORTHOPAEDIC IMPLANTS

(75) Inventors: Brion R. Mimnaugh, North Webster, IN (US); Michael E. Hawkins, Columbia City, IN (US); Jacque R. Wilson, Fort Wayne, IN (US)

(73) Assignee: Zimmer, Inc., Warsaw, IN (US)

( * ) Notice: Subject to any disclaimer, the term of this patent is extended or adjusted under 35 U.S.C. 154(b) by 269 days.

(21) Appl. No.: 11/095,228

(22) Filed: Mar. 31, 2005

(65) Prior Publication Data

US 2006/0223905 A1  Oct. 5, 2006

(51) Int. Cl.
*B29C 71/02* (2006.01)
*B29C 71/04* (2006.01)
*B29C 71/00* (2006.01)
*C08J 3/00* (2006.01)
*C08J 3/28* (2006.01)

(52) U.S. Cl. .................. 264/346; 522/150; 522/161; 522/157; 264/405; 264/425; 264/340; 264/345; 623/11.11; 623/16.11; 526/352; 526/352.2; 523/115

(58) Field of Classification Search ................ 522/157, 522/161, 125, 150, 113, 114, 115; 523/115; 526/352, 352.2; 623/18, 22, 11.11, 16.11; 264/340, 345, 405, 425, 346
See application file for complete search history.

(56) References Cited

U.S. PATENT DOCUMENTS

| | | | |
|---|---|---|---|
| 3,297,641 A | 1/1967 | Werber et al. | |
| 3,352,818 A | 11/1967 | Meyer et al. | |
| 3,758,273 A | 9/1973 | Johnston et al. | |
| 5,037,928 A | 8/1991 | Li et al. | |
| 5,160,464 A | 11/1992 | Ward et al. | |
| 5,414,049 A | 5/1995 | Sun et al. | |
| 5,449,745 A | 9/1995 | Sun et al. | |
| 5,466,530 A | 11/1995 | England et al. | |
| 5,543,471 A | 8/1996 | Sun et al. | |
| 5,879,400 A | 3/1999 | Merrill et al. | |
| 6,165,220 A | 12/2000 | McKellop et al. | |
| 6,228,900 B1 | 5/2001 | Shen et al. | |
| 6,365,089 B1 | 4/2002 | Krebs et al. | |
| 6,500,386 B1 * | 12/2002 | Burstein ..................... 422/22 | |
| 6,503,439 B1 | 1/2003 | Burstein | |
| 6,852,772 B2 * | 2/2005 | Muratoglu et al. .......... 522/161 | |
| 7,160,492 B2 * | 1/2007 | King ........................ 264/101 | |
| 2003/0149125 A1 * | 8/2003 | Muratoglu et al. .......... 522/150 | |
| 2005/0124718 A1 * | 6/2005 | Muratoglu et al. .......... 522/161 | |

FOREIGN PATENT DOCUMENTS

| | | |
|---|---|---|
| EP | 0722973 A1 | 7/1986 |
| WO | WO9729895 A1 | 8/1997 |
| WO | WO 98/01085 | 1/1998 |
| WO | WO0076754 A1 | 12/2000 |
| WO | WO02058912 A1 | 8/2002 |

OTHER PUBLICATIONS

Super Low Wear Cross-Linked UHMWPE by Heavy High-Dose Gamma Radiation, Oonishi, H., Kuno, M., Idada, Y., Fujisawa, A., and Masuda, S., 1996, WPOA 2nd Congress of Hip Section.
Journal of Polymer Science, Part B, Polymer Letters, "The Influence of the Temperature of Irradiation on the formation of Polymer Networks", D. T. Turner vol. 1, No. 2, Feb. 1963, p. 101.
The Improvement of Polyethylene Prostheses Through Radiation Crosslinking, T.A. du Plessis, C. J. Grobbelaar, and F. Marais, Radiat. Phys. Chem. 1977, vol. 9, pp. 647-652.
The Friction and Wear Behavior of Irradiated Very High Molecular Weight Polyethylene, C. Shen and J.H. Dumbleton, Wear 30, (1974) pp. 349-364.
Crystalline and Supermolecular Structures in Linear Polyethylene Irradiated with Fast Electrons, G. Gielenz and B. J. Jungnickel, Colloid & Polymer Science 260, pp. 742-753 (1982).
Improved Mechanical Behaviour in Ultra-High Modulus Polyethylenes by Controlled Cross-Linking, D. W. Woods, W. K. Busfield and I.M. Ward, Plastics and Rubber Processing and Applications 5 (1985) pp. 157-164.
Irradiation of Ultrahigh-Molecular-Weight Polyethylene, A. Shinde and R. Salovey, Journal of Polymer Science: Polymer Physics Edition, vol. 23, 1681-1689 (1985).
Ionizing Irradiation for Sterilization and Modification of High Molecular Weight Polyethylenes, Robert M. Streicher, Plastics and Rubber Processing and Applications vol. 10, (1988) No. 4, pp. 221-229.
Influence of Ionizing Irradiation in Air and Nitrogen for Sterilization of Surgical Grade Polyethylene for Implants, R. M. Streicher, Radiat. Phys. Chem, vol. 31, Nos. 4-6, pp. 693-698, 1988.
Improvement of Polyethylene by Irradiation in Artificial Joints, H. Oonishi, Y. Takayama, and E. Tsuri, Radiat. Phys. Chem. vol. 39, No. 6, pp. 495-504, 1992.
The Radiation Chemistry of Polyethylene. IX. Temperature Coefficient of Cross-Linking and Other Effects, H. Y. Kang, O. Saito, and M. Dole, Journal of the American Chemical Society, 89:9, Apr. 26, 1967, pp. 1980-1986.
The Radiation Improvement of Polyethylene Prostheses, A Preliminary Study, C. J. Grobbelaar, T. A. Du Plessis, F. Marais, The Journal of Bone and Joint Surgery, vol. 60-B, No. 3, Aug. 1978, pp. 370-374.
The Effects of Radiation Sterilization on the Properties of Ultrahigh Molecular Weight Polyethylene, H. J. Nusbaum and R. M. Rose, Journal of Biomedical Materials Research, vol. 13, pp. 557-576 (1979).
Radiation Sterilization and the Wear Rate of Polyethylene, R. M. Rose, E. V. Goldfarb, E. Ellis, and A. N. Crugnola, Journal of Orthopadedic Research, pp. 393-400, 1984 Orthopaedic Research Society.
Cross-Linking of Ultra-High Molecular Weight Polyethylene in the melt by means of Electron Beam Irradiation, D. J. Dijkstra, W. Hoogsteen, and A. J. Pennings, Polymer, 1989, vol. 30, May, pp. 866-873.
Effect of .gamma. Irradiation on the Fricition and Wear of Ultrahigh Molecular Weight Polyethylene, William R. Jones, Jr., and William F. Hady, Wear, 70 (1981) 77-92.
The International Search Report mailed on Nov. 2, 2006 in related International application No. PCT/US2006/004652.
The IPRP issued in related International application No. PCT/US2006/004652.

* cited by examiner

*Primary Examiner*—Sanza L McClendon
(74) *Attorney, Agent, or Firm*—Baker & Daniels LLP

(57) ABSTRACT

A method is provided for annealing a polymer for an orthopaedic implant by immersing the polymer in a liquid bath.

33 Claims, 2 Drawing Sheets

LIQUID BATH ANNEALING OF POLYMERS FOR ORTHOPAEDIC IMPLANTS

FIELD OF THE INVENTION

The present invention relates to a method for enhancing the mechanical properties of orthopaedic polymers. More particularly, the present invention relates to a method for annealing orthopaedic polymers.

BACKGROUND

Polymers are commonly used as bearing materials paired with an opposing component in orthopaedic implants such as hips and knees. Typically, ultra high molecular weight polyethylene (UHMWPE) is paired with a complimentary metal bearing surface. It is known that irradiating certain polymers, such as UHMWPE, can cause changes in their chemical and mechanical properties. For example, when UHMWPE is subjected to gamma irradiation in the range of 25-37 kGy, it has been observed that with time it can change color and become embrittled. This is of interest in the medical device field since such an irradiation dose is within the range of commonly used sterilization processes. The general belief is that the changes in material properties are due to competing reaction pathways, one being crosslinking within and between polymer chains, and another being oxidation. Crosslinking results in an increase in molecular weight of the polymer, while oxidation results in decreasing molecular weight.

High energy, ionizing radiation, such as gamma or electron beam radiation, breaks molecular bonds, called chain scission, and creates free radicals that are highly reactive species. The severed chains can recombine, crosslink with adjacent chains, or combine with other species such as oxygen. In the presence of oxygen, the severed chain is more likely to form an oxygenated species which is then not able to form crosslinks or recombine, resulting in a reduction of molecular weight. This reduction of molecular weight causes a reduction in mechanical properties and embrittlement. Some of the free radicals formed are not capable of reacting due to their location in the polymer structure and thus can persist in the polymer for long periods. The migration of species, such as oxygen, over long periods of time to these isolated free radicals can result in further oxidation and molecular weight reduction, with a subsequent time dependent degradation of properties.

Notwithstanding the potential for detrimental reactions that have been observed in radiation sterilized polymers, some investigators have proposed using even higher doses of radiation to create even more crosslinking to increase the abrasion resistance of polymers. Various investigators have proposed this type of aggressive crosslinking of UHMWPE orthopaedic implants. Crosslinking occurs in polymers when adjacent polymer chains form c-c bonds. Such crosslinking acts to prevent the polymer chains from being pulled or pushed apart. The degree of crosslinking of a material is a function of the radiation dose it receives. The total dose received depends on the penetrative properties of the radiation in the material being treated and the exposure time to the radiation source.

However the polymer is crosslinked, some investigators have proposed ways to reduce oxidation and/or increase crosslinking. Their methods generally involve maintaining the article being irradiated in an oxygen free environment. For example, Shen and Dumbleton teach that gamma irradiation in an argon atmosphere results in a high percentage of crosslinking and improves the wear performance of polyethylene. C. Shen and J. H. Dumbleton, The Friction and Wear Behavior of Irradiated Very High Molecular Weigh Polyethylene, 30 Wear, 349 (1974). Grobbelaar et al. teach that by gamma irradiating polyethylene prostheses in a reactive organic atmosphere containing acetylene, enhanced crosslinking at the surface is achieved which results in reduced deformation while maintaining excellent abrasion resistance. Grobbelaar et al., The Radiation Improvement of Polyethylene Prostheses: A Preliminary Study, 60-B:3 JBJS 370 (1978).

Other investigators have taught free radical elimination via post irradiation processing. Kang et al. teach that crosslinking polyethylene with gamma irradiation is enhanced by raising the temperature of the polyethylene during irradiation and furthermore that free radicals can be removed by annealing the polyethylene after irradiation. Kang et al., The Radiation Chemistry of Polyethylene. IX Temperature Coefficient of Cross-Linking and Other Effects, 89:9 Journal of American Chemical Society 1980 (1967). Sun et al. likewise teach in U.S. Pat. No. 5,414,049 that free radicals may be removed by heating the irradiated article. These post irradiation processes can take several days to achieve the desired reduction in free radicals.

SUMMARY

The present invention provides a method of treating orthopaedic implants including a polymer by immersing the polymer in a liquid bath to anneal the polymer.

In one aspect of the invention, a method of treating a polymer for an orthopaedic implant includes irradiating the polymer and immersing the polymer in a liquid bath to anneal the polymer.

In another aspect of the invention, the annealing temperature is greater than or equal to the melt temperature of the polymer.

In another aspect of the invention, the liquid bath comprises one or more liquids selected from the list consisting of water, glycerin, and oil.

In another aspect of the invention, the method further includes molding a polymer to a porous substrate prior to irradiating the polymer.

In another aspect of the invention, immersing the polymer includes immersing the polymer sequentially in a series of progressively warmer baths to control the rate at which the polymer is raised to the annealing temperature.

In another aspect of the invention, the method further includes immersing the polymer in a liquid bath to cool the polymer from the annealing temperature.

BRIEF DESCRIPTION OF THE DRAWINGS

Various examples of the present invention will be discussed with reference to the appended drawings. These drawings depict only illustrative examples of the invention and are not to be considered limiting of its scope.

DESCRIPTION OF THE ILLUSTRATIVE EXAMPLES

Figure 1:
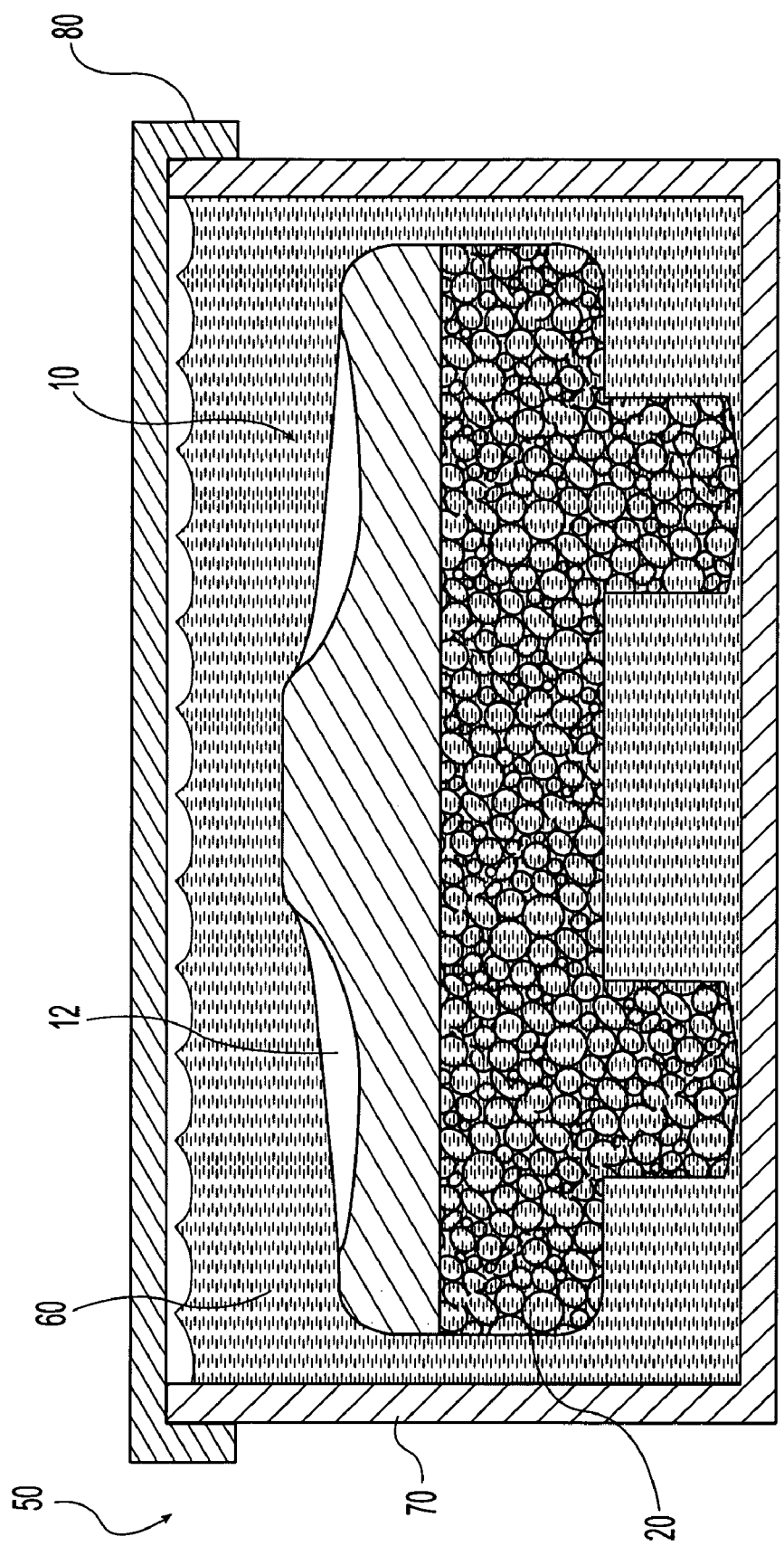
FIG. 1 is a cross sectional view of an illustrative implant undergoing an annealing process according to the present invention.
Figure 2:
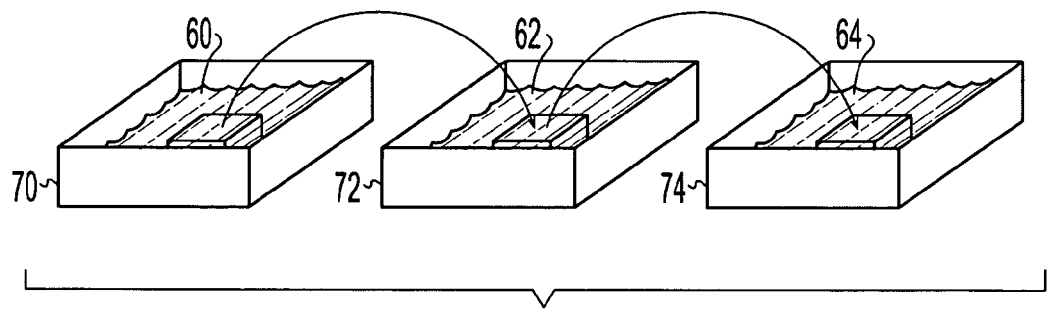
FIG. 2 is a schematic drawing showing an implant undergoing the annealing process of FIG. 1 by sequential immersion.

FIG. 1 depicts an illustrative orthopaedic implant in the form of a tibial knee implant 10 having polymer condylar articular regions 12 for articulating engagement with a femoral knee component (not shown). The polymer 12 is irradiated to sterilize it and/or to induce property enhancing crosslinking. For sterilization, the polymer 12 may be exposed to a radiation dose of from 25 to 37 kGy. For crosslinking the polymer 12 may be exposed to a radiation dose of from 25 to 300 kGy, more preferably between 45 and 115 kGy, and still more preferably 45 and 85 kGy. The polymer 12 may be irradiated using gamma irradiation, electron beam irradiation, or other suitable forms of irradiation. For example, the polymer 12 may be placed in the vicinity of a gamma source for a period of time to achieve the desired dose. Typically a cobalt 60 gamma source will produce a dose of 25 to 37 kGy in approximately 24 hours of exposure. In another example, an electron beam source may be directed toward the polymer 12 as it travels past the source on a conveyor. Electron beam irradiation of a polymer such as UHMWPE will vary in the depth of penetration depending on the energy level of the accelerated beam. The greater the energy level, the greater the depth of penetration. For example, energy levels can range from 1 to 20 MeV at a beam power of from 1 to 120 kW. Typical commercial electron beam sources use a 10 MeV beam at a beam power of 60 kW. An electron beam of 10 MeV and 60 kW beam power will penetrate UHMWPE to a depth of approximately 4 to 5.5 cm. Typically, an electron beam of 10 MeV and 60 kW beam power can produce a dose of from 45 to 85 kGy in UHMWPE in a few seconds of exposure.

After the polymer 12 is irradiated, it is annealed by maintaining the polymer 12 at an elevated temperature to speed the reaction of any free radicals present in the polymer. The present investigators have discovered that the time to reach an appropriate annealing temperature is reduced by heating the polymer 12 in a liquid bath 50 including a liquid 60 filled container 70 as shown in FIG. 1. For example, the present investigators have found that parts heated in a dry oven can take up to 25 hours to heat completely to their centers to an annealing temperature of 150° C. and an additional 4 or more hours at that temperature to eliminate the free radicals. Conversely, parts heated in a liquid bath 50 take less than an hour to reach the annealing temperature. Thus, the present invention can drastically reduce cycle times. Furthermore, the liquid bath can exclude atmospheric oxygen from the surface of the polymer 12 during annealing.

The polymer 12 may be placed in the liquid 60 at room temperature and the liquid 60 and polymer 12 heated to the annealing temperature, held for the required time, and then cooled. Preferably, the liquid 60 is maintained at an elevated temperature and the polymer 12 is immersed in the pre-heated liquid 60. This reduces the annealing time and saves energy used to heat the liquid 60 since there is no need to cycle the temperature of the liquid 60. After the polymer 12 is annealed, it may be removed from the liquid 60 and allowed to cool in the atmosphere. Alternatively, the liquid bath 50 may be cooled while the implant remains immersed to cool the polymer 12 according to a prescribed cooling cycle. Also alternatively, the polymer 12 may be cooled by placing it in another liquid 62 filled container 72 maintained at a lower temperature. The polymer 12 is preferably immersed after it is irradiated. However, it is within the scope of the invention for the polymer 12 to be immersed prior to irradiation with annealing occurring after irradiation.

The heating and cooling times and temperatures may be controlled by providing several liquid 60, 62, 64 filled containers 70, 72, 74 having liquids 60, 62, 64 maintained at different temperatures. The polymer 12 can then be heated by moving it between progressively warmer liquids 60, 62, 64. The rate of heating can be controlled by how long the polymer 12 is in each liquid 60, 62, 64 and by the temperature difference between a particular liquid 60, 62, 64 and the polymer 12. Similarly, the polymer 12 can be cooled by moving it between progressively cooler liquids. By maintaining one or more liquid 60, 62, 64 filled containers 70, 72, 74 each at an approximately constant temperature, the polymer 10 may be efficiently annealed in a continuous process wherein one or more pieces are moved into and out of one or more liquid baths without the need to assemble a batch to be heated and cooled together according to a prescribe time-temperature curve. This saves time and energy in not having to cycle the liquid baths.

Figure 3:
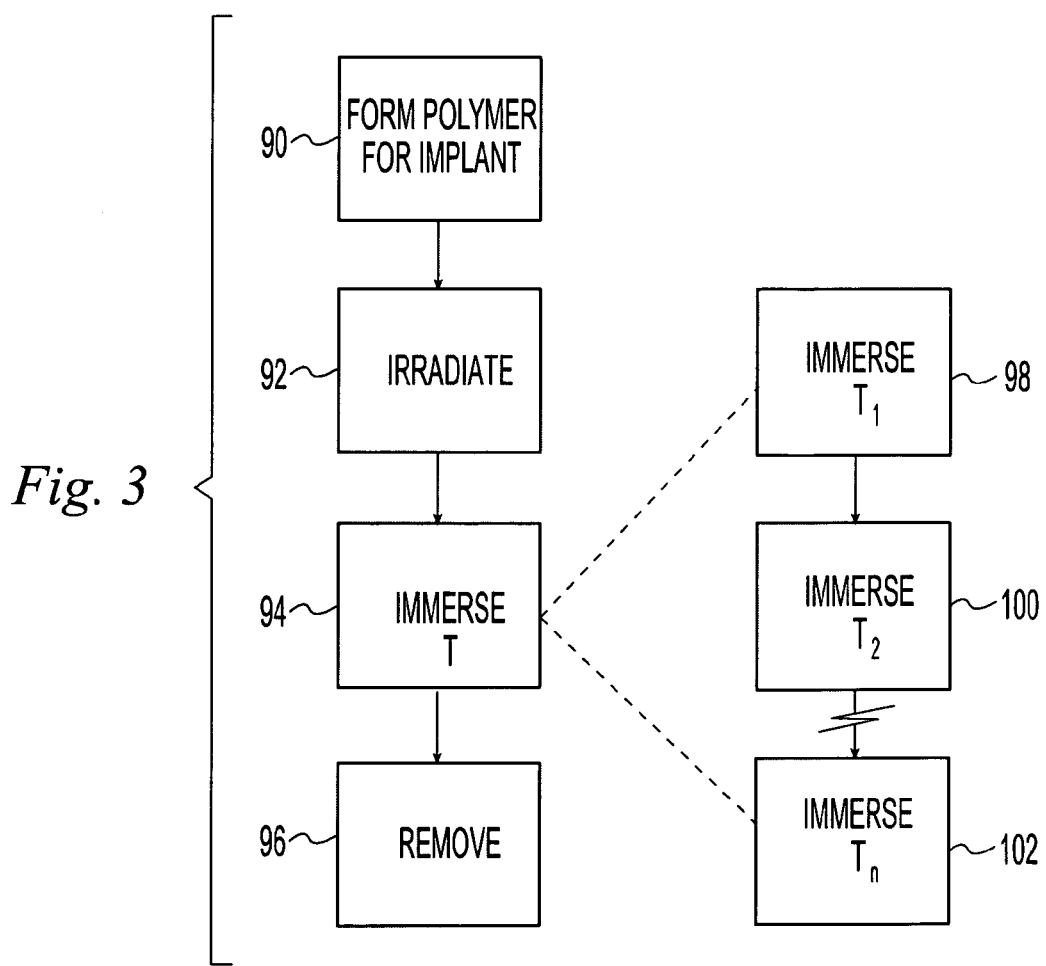
FIG. 3 is a diagram illustrating the annealing process of FIGS. 1 and 2.

FIG. 3 illustrates the steps of the liquid bath annealing process. The polymer 12 is formed 90 for the implant 10. At this stage the polymer 12 may be in the form of rough stock such as a bar, billet, block, disc, or other rough form. Alternatively, the polymer 12 may be formed into a near net shape in which it is approximately shaped into the final implant form with some forming still to be performed after annealing. Also alternatively, the polymer 12 may be formed to its final shape and/or include other components such as the non-polymeric substrate 20 as shown in FIG. 1. The polymer 12 is then irradiated 92. After irradiation 92, the polymer 12 is immersed 94 in a liquid bath at temperature "T" to anneal the polymer 12. Temperature "T" may be the final annealing temperature or it may be a lower temperature and the liquid bath may be heated to the annealing temperature after the polymer 12 is immersed. Finally, the polymer 12 is removed 96 from the liquid bath. Alternatively, as shown by blocks 98, 100, and 102, the step of immersing the polymer 12 may include immersing the implant sequentially in any number of baths at different temperatures. In addition to immersing the polymer 12 to heat it, the polymer 12 may be immersed to cool it. Also alternatively, steps 92 and 94 may be reversed so that the polymer 12 is immersed prior to irradiation.

Higher annealing temperatures will tend to accelerate the reaction of free radicals. The upper limit on the annealing temperature will vary depending on the particular polymer 12. Polymers may be annealed below their melting temperature. However, annealing in the melt, where possible, greatly facilitates the reaction of free radicals. Some polymers will change shape when they are heated to their melting point whereas others will maintain their shape. For example, UHMWPE is a semicrystalline polymer that has a melting temperature defined as the temperature at which the crystalline portion of the polymer melts. The melt temperature for UHMWPE is approximately 140° C. and is characterized by the UHMWPE becoming translucent. However, UHMWPE remains substantially dimensionally stable and annealing in the melt is feasible for UHMWPE. Suitable annealing temperatures for UHMWPE are in the range of 130-250° C., preferably 140-180° C., more preferably 150-165° C.

Useful liquids 60 for annealing the polymer 12 preferably have boiling points at least as high as the desired annealing temperature. Furthermore, the liquids preferably do not render the implant toxic or degrade the implant. In particular, liquids having large molecular structures are useful as they may have limited penetration into the implant. Some suitable liquids include oils, water, glycerin, and/or other suitable materials. For example, water and glycerin solutions may be used as an annealing liquid 60. Water has a boiling point of 100° C. and glycerin has a boiling point of 290° C. By varying the amounts of water and glycerin, solutions may be obtained that have boiling points ranging from 100° C. to 290° C. Thus, for example, if annealing is to be carried out at 160° C., a water and glycerin solution can be produced that has a boiling point greater than 160° C. at atmospheric pressure such that the solution can be maintained at 160° C. and the polymer 12 may be freely added and removed as required. Alternatively, liquids may be used that have boiling points below the desired annealing temperature. For example, water may be used. After the polymer 12 is placed in the liquid 60, a lid 80 may be placed over the container 70 and the temperature raised to the desired annealing temperature. The lid 80 will allow the pressure in the container 70 to increase so that the temperature of the liquid 60 may be increased above its atmospheric boiling point. Oils may include mineral oil, vegetable oils, and/or other suitable oils.

Additives can also be added to the fluid 60 to further aid the annealing process and/or enhance the polymer 12. For example, anti-bacterial agents, free radical scavengers, and/or other suitable additives may be added to the liquid. Examples of anti-bacterial agents are tetracycline, gentamicin, and other antibiotics. An example of a free radical scavenger is vitamin E.

Another advantage of the present liquid annealing process is the ability of the liquid to penetrate into small spaces to uniformly heat the implant 10 and exclude atmospheric oxygen from surfaces that cannot easily be machined away subsequent to irradiation should they become oxidized. For example, the illustrative implant 10 includes an optional substrate 20 to which the polymer 12 is attached. The substrate 20 may be formed from metals, polymers, ceramics, and/or other suitable materials. Preferably the substrate includes a porous structure on its lower surface 22 to promote tissue ingrowth to secure the substrate to tissue and a porous structure on its upper surface 24 such that the condylar articular regions 12 may be attached to the substrate by molding the polymer into the pores of the substrate 20 so that the polymer interdigitates with the substrate 20. The substrate 20 may be produced by consolidating fibers, consolidating beads, etching, machining, dissolving away fillers, and/or other suitable processes. In applications where bony ingrowth is desired, such as the implant 10 of FIG. 1, the substrate preferably includes a porous metal. For example, the illustrative porous substrate includes a tantalum metal porous surface having a structure similar to that of natural trabecular bone. Such a material is described in U.S. Pat. No. 5,282,861 entitled "OPEN CELL TANTALUM STRUCTURES FOR CANCELLOUS BONE IMPLANTS AND CELL AND TISSUE RECEPTORS", issued to R. B. Kaplan and assigned to Ultramet. The material is fabricated of tantalum using vapor deposition. This material has been sold by Implex Corporation of Allendale, N.J., under the tradename HEDROCEL. Zimmer, Inc., with manufacturing facilities in Warsaw, Ind., sells a line of surgical implants incorporating this trabecular metal technology.

Irradiation of the illustrative implant 10 after molding will result in areas 14 of the polymer along the polymer-to-substrate interface that are inaccessible to post irradiation machining operations. Thus, removal of an oxidized layer at this interface by machining is not possible. However, liquid annealing according to the present invention results in the annealing liquid 60 penetrating to the polymer 14 at the interface to block atmospheric oxygen and to provide uniform heating of the interface.

Although an example of a method for annealing a polymer for an orthopaedic implant has been described and illustrated in detail, it is to be understood that the same is intended by way of illustration and example only and is not to be taken by way of limitation. In particular, while the illustrative embodiments have been directed to an UHMWPE tibial knee component, the method is suitable for any polymer for any orthopaedic application in which heating will lead to a desirable change in properties. Accordingly, variations in and modifications to the method will be apparent to those of ordinary skill in the art, and the following claims are intended to cover all such modifications and equivalents.

What is claimed is:

1. A method of treating a polymer for an orthopaedic implant, the method comprising:
   irradiating the polymer; and
   immersing and progressively heating the polymer in an inert liquid bath to anneal the polymer.

2. The method of claim 1 wherein the polymer is immersed in the liquid bath to heat the polymer to a predetermined annealing temperature and maintain the polymer at the predetermined annealing temperature for a predetermined annealing time.

3. The method of claim 1 further comprising forming the polymer into a near net shape form prior to irradiating the polymer.

4. The method of claim 1 further comprising forming the polymer into its final implant shape prior to irradiating the polymer.

5. The method of claim 1 further comprising attaching the polymer to a non-polymeric substrate prior to irradiation.

6. The method of claim 1 wherein the polymer comprises UHMWPE.

7. The method of claim 6 wherein the polymer is irradiated at an irradiation dose is between 25 kGy and 300 kGy.

8. The method of claim 6 wherein the polymer is irradiated at an irradiation dose between 45 kGy and 116 kGy.

9. The method of claim 6 wherein the polymer is irradiated at an irradiation dose between 45 kGy and 85 kGy.

10. The method of claim 6 wherein an annealing temperature of the polymer is between 130.degree. C. and 250, degree. C.

11. The method of claim 6 wherein an annealing temperature of the polymer is between 140.degree. C. and 180.degree. C.

12. The method of claim 6 wherein the an annealing temperature of the polymer is between 150.degree. C. and 165.degree. C.

13. The method of claim 1 wherein an annealing temperature of the polymer is greater than or equal to a melt temperature of the polymer.

14. The method of claim 1 wherein the liquid bath comprises one or more liquids selected from the list consisting of water, glycerin, and oil.

15. A method of treating a polymer for an orthopaedic implant, the method comprising:
   irradiating the polymer; and
   immersing the polymer in an inert liquid bath to anneal the polymer, wherein the liquid bath comprises a mixture of water and glycerin.

16. The method of claim 1 wherein the liquid bath comprises a liquid having a boiling point at atmospheric pressure greater than the annealing temperature of the polymer.

17. The method of claim 1 wherein the liquid bath comprises a liquid having a boiling point at atmospheric pressure less than an annealing temperature of the polymer and the liquid bath is pressurized to suppress boiling and allow the liquid bath to reach a temperature greater than its boiling point at atmospheric pressure.

18. A method of treating a polymer for an orthopaedic implant, the method comprising:
    molding a polymer to a porous substrate prior to irradiating the polymer;
    irradiating the polymer; and
    immersing the polymer in an inert liquid bath to anneal the polymer.

19. The method of claim 18 wherein UHMWPE is molded into a porous tantalum substrate.

20. The method of claim 1 wherein immersing and progressively heating the polymer comprises immersing the polymer sequentially in a series of progressively warmer baths to control the rate at which the polymer is raised to the annealing temperature.

21. A method of treating a polymer for an orthopaedic implant, the method comprising:
    irradiating the polymer;
    immersing the polymer in an inert liquid bath to anneal the polymer; and
    immersing the polymer in a liquid bath to cool the polymer from an annealing temperature of the polymer.

22. The method of claim 21 wherein immersing the polymer in a liquid bath to cool the polymer comprises immersing the polymer sequentially in a series of progressively cooler baths to control the rate at which the polymer is cooled.

23. A method of treating a polymer for an orthopaedic implant, the method comprising:
    irradiating the polymer; and
    immersing the polymer in an inert liquid bath to anneal the polymer, wherein the liquid bath includes an antibiotic.

24. The method of claim 15 wherein the polymer is immersed in the liquid bath to progressively heat the polymer to a predetermined annealing temperature and maintain the polymer at the predetermined annealing temperature for a predetermined annealing time.

25. The method of claim 15 wherein the polymer comprises UHMWPE.

26. The method of claim 18 wherein an annealing temperature of the polymer is greater than or equal to a melt temperature of the polymer.

27. The method of claim 18 wherein the liquid bath comprises a liquid having a boiling point at atmospheric pressure greater than an annealing temperature of the polymer.

28. The method of claim 21 wherein the polymer is immersed in the liquid bath to progressively heat the polymer to a predetermined annealing temperature and maintain the polymer at the predetermined annealing temperature for a predetermined annealing time.

29. The method of claim 21 wherein the polymer comprises UHMWPE.

30. The method of claim 21 wherein the liquid bath comprises a liquid having a boiling point at atmospheric pressure greater than an annealing temperature of the polymer.

31. The method of claim 23 wherein the polymer is immersed in the liquid bath to progressively heat the polymer to a predetermined annealing temperature and maintain the polymer at the predetermined annealing temperature for a predetermined annealing time.

32. The method of claim 23 wherein the polymer comprises UHMWPE.

33. The method of claim 23 wherein the liquid bath comprises a liquid having a boiling point at atmospheric pressure greater than an annealing temperature of the polymer.

* * * * *